United States Patent
Hou et al.

(10) Patent No.: US 11,021,712 B1
(45) Date of Patent: Jun. 1, 2021

(54) MIRNA MIMICS AND USES THEREOF

(71) Applicants: Jianghui Hou, St. Louis, MO (US); Yong-feng Gong, St. Louis, MO (US)

(72) Inventors: Jianghui Hou, St. Louis, MO (US); Yong-feng Gong, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 16/561,602

(22) Filed: Sep. 5, 2019

Related U.S. Application Data

(60) Provisional application No. 62/728,089, filed on Sep. 7, 2018.

(51) Int. Cl.
| | |
|---|---|
| *A61K 48/00* | (2006.01) |
| *C07H 21/04* | (2006.01) |
| *C12N 15/113* | (2010.01) |
| *A61P 3/10* | (2006.01) |

(52) U.S. Cl.
CPC ............ *C12N 15/1138* (2013.01); *A61P 3/10* (2018.01); *C12N 2310/141* (2013.01); *C12N 2310/321* (2013.01); *C12N 2310/351* (2013.01); *C12N 2310/3515* (2013.01)

(58) Field of Classification Search
CPC ............ C12N 15/113; C12N 2310/141; A61K 31/713
See application file for complete search history.

(56) References Cited

U.S. PATENT DOCUMENTS

| | | | |
|---|---|---|---|
| 9,376,681 B2 | 6/2016 | Montgomery et al. | |
| 2012/0259001 A1* | 10/2012 | Khvorova | C12N 15/111 514/44 A |
| 2016/0251656 A1* | 9/2016 | Berriel Diaz | A61P 3/10 514/44 A |

OTHER PUBLICATIONS

Massart et al., Diabetes, vol. 66, Jul. 2017, pp. 1807-1818.*
He et al. (Molecular Endocrinology, 21, 11, 2785-2794).*
Brenner BM, Cooper ME, De Zeeuw D, et al. Effects of losartan on renal and cardiovascular outcomes in patients with type 2 diabetes and nephropathy. N Engl J Med. 2001;345(12):861-869. doi:10.1056/NEJMoa011161.
Chua SC, Chung WK, Wu-Peng XS, et al. Phenotypes of Mouse diabetes and Rat fatty Due to Mutations in the OB (Leptin) Receptor. Science. 1996;271(5251):994-996. doi:10.1126/science. 271.5251.994.
Clément K, Vaisse C, Lahlou N, et al. A mutation in the human leptin receptor gene causes obesity and pituitary dysfunction. Nature. 1998;392(6674):398-401. doi:10.1038/32911.
Collier CA, Bruce CR, Smith AC, Lopaschuk G, Dyck DJ. Metformin counters the insulin-induced suppression of fatty acid oxidation and stimulation of triacylglycerol storage in rodent skeletal muscle. Am J Physiol Endocrinol Metab. 2006;291(1):E182-189. doi:10.1152/ajpendo.00272.2005.
Elsas LJ, Endo F, Strumlauf E, Elders J, Priest JH. Leprechaunism: an inherited defect in a high-affinity insulin receptor. Am J Hum Genet. 1985;37(1):73-88.
Hundal RS, Krssak M, Dufour S, et al. Mechanism by which metformin reduces glucose production in type 2 diabetes. Diabetes. 2000;49(12):2063-2069. doi:10.2337/diabetes.49.12.2063.
Kirpichnikov D, Mcfarlane SI, Sowers JR. Metformin: an update. Ann Intern Med. 2002;137(1):25-33. doi:10.7326/0003-4819-137-1-200207020-00009.
Kriegel AJ, Liu Y, Fang Y, Ding X, Liang M. The miR-29 family: genomics, cell biology, and relevance to renal and cardiovascular injury. Physiol Genomics. 2012;44(4):237-244. doi:10.1152/physiolgenomics.00141.2011.
Lin C-L, Lee P-H, Hsu Y-C, et al. MicroRNA-29a Promotion of Nephrin Acetylation Ameliorates Hyperglycemia-Induced Podocyte Dysfunction. J Am Soc Nephrol. 2014;25(8):1698-1709. doi:10.1681/ASN.2013050527.
Müller-Wieland D, Van Der Vorm ER, Streicher R, et al. An in-frame insertion in exon 3 and a nonsense mutation in exon 2 of the insulin receptor gene associated with severe insulin resistance in a patient with Rabson-Mendenhall syndrome. Diabetologia. 1993;36(11):1168-1174. doi:10.1007/bf00401062.
Ogawa W, Iwamoto K, Mori H, et al. Two related cases of type A insulin resistance with compound heterozygous mutations of the insulin receptor gene. Diabetes Res Clin Pract. 2009;83(3):e75-7. doi:10.1016/j.diabres.2008.12.002.
Slusarz A, Pulakat L. The two faces of miR-29. J Cardiovasc Med (Hagerstown). 2015;16(7):480-490. doi:10.2459/JCM.0000000000000246.
Tonneijck L, Muskiet MHA, Smits MM, et al. Glomerular Hyperfiltration in Diabetes: Mechanisms, Clinical Significance, and Treatment. J Am Soc Nephrol. 2017;28(4):1023-1039. doi:10.1681/ASN.2016060666.

* cited by examiner

*Primary Examiner* — Amy H Bowman

(57) ABSTRACT

Among the various aspects of the present disclosure is the provision of miRNA mimics and uses thereof. An aspect of the present disclosure provides for compositions of miRNA mimic molecules and methods of treating metabolic disorders using miRNA mimic molecules.

11 Claims, 5 Drawing Sheets

Specification includes a Sequence Listing.

MIRNA MIMICS AND USES THEREOF

CROSS-REFERENCE TO RELATED APPLICATIONS

This application claims priority from U.S. Provisional Application Ser. No. 62/728,089 filed on 7 Sep. 2018, which is incorporated herein by reference in its entirety.

STATEMENT REGARDING FEDERALLY SPONSORED RESEARCH OR DEVELOPMENT

This invention was made with government support under DK084059 awarded by the National Institutes of Health. The government has certain rights in the invention.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present disclosure generally relates to compositions and methods for treatment of metabolic disorders.

SUMMARY OF THE INVENTION

Among the various aspects of the present disclosure is the provision of microRNA (miRNA or miR) mimics and uses thereof.

An aspect of the present disclosure provides for a method of increasing gene expression levels of insulin receptor (INSR) in a subject in need thereof.

In some embodiments, the method comprises administering to the subject a therapeutically effective amount of a pharmaceutical composition comprising a miR-29 mimic molecule, wherein the miR-29 mimic molecule has INSR gene expression activity.

In some embodiments, the miR-29 mimic molecule comprises a working strand sequence comprising UAGCACCAUCUGAAAUCGGUUUU (SEQ ID NO: 1).

In some embodiments, the miR-29 mimic molecule comprises a passenger strand.

In some embodiments, the passenger strand optionally comprises a sequence selected from AACCGAUUUCuuuUGGUGCUAUU (SEQ ID NO: 2).

In some embodiments, the miR-29 mimic molecule comprises a miR-29a (SEQ ID NO: 3), a miR-29b (SEQ ID NO: 4), ora miR-29c (SEQ ID NO: 5), or an analogue thereof.

In some embodiments, the passenger strand comprises a modification to increase stability or a modification to enhance cellular uptake.

In some embodiments, the modification to increase stability comprises 2'-O-methylation.

In some embodiments, the modification to enhance cellular uptake comprises a cholesterol conjugated to the 3'-end of the passenger strand.

In some embodiments, the method comprises a carrier conjugated to the miR-29 mimic molecule.

In some embodiments, the carrier comprises a polyethylenimine (PEI), a polycationic polymer, or amphiphilic non-viral carrier.

In some embodiments, the subject has a metabolic disorder selected from diabetic nephropathy (DN), diabetes mellitus (DM), insulin deficiency, or insulin resistance.

In some embodiments, the therapeutically effective amount corrects albuminuria, corrects polyuria, corrects glucose tolerance, or corrects insulin tolerance in the subject.

In some embodiments, the therapeutically effective amount reduces water intake, reduces urine output, reduces serum glucose levels, reduces insulin sensitivity, or reduces urinary albumin levels in a subject.

In some embodiments, the metabolic disorder does not comprise diabetic fibrosis.

Another aspect of the present disclosure provides for a pharmaceutical composition comprising a miR-29 mimic molecule comprising and a carrier conjugated to the miR-29 mimic molecule.

In some embodiments, the miR-29 mimic molecule comprises a working strand sequence comprising UAGCACCAUCUGAAAUCGGUUUU (SEQ ID NO: 1).

In some embodiments, the miR-29 mimic molecule comprises a passenger strand, wherein the passenger strand optionally comprises a sequence selected from AACCGAUUUCuuuUGGUGCUAUU (SEQ ID NO: 2).

In some embodiments, the miR-29 mimic molecule comprises a miR-29a (SEQ ID NO: 3), a miR-29b (SEQ ID NO: 4), or a miR-29c (SEQ ID NO: 5), or an analogue thereof.

In some embodiments, the passenger strand comprises a modification to increase stability or a modification to enhance cellular uptake.

In some embodiments, the modification to increase stability comprises 2'-O-methylation.

In some embodiments, the modification to enhance cellular uptake comprises a cholesterol conjugated to the 3'-end of the passenger strand.

In some embodiments, the pharmaceutical composition comprises a carrier conjugated to the miR-29 mimic molecule.

In some embodiments, the carrier comprises a polyethylenimine (PEI), a polycationic polymer, or amphiphilic non-viral carrier.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1:
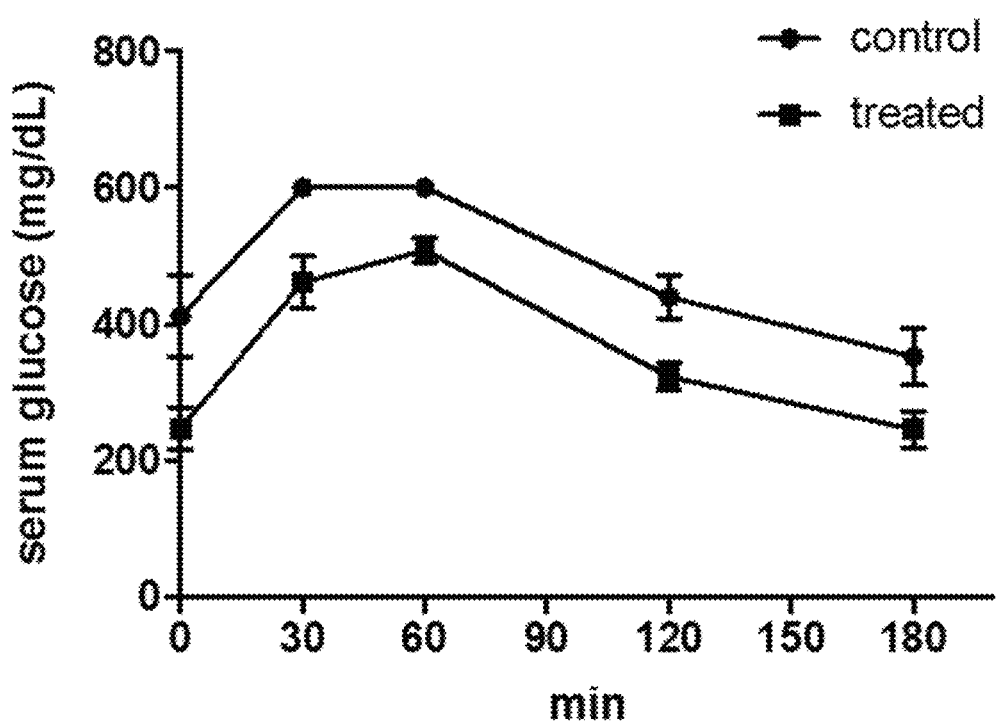
FIG. 1 illustrates a serum glucose tolerance test. Mice treated with miR-29 mimics showed reduced serum glucose levels after fasting (time 0) and after oral supplementation of glucose, compared to untreated control animals. N=5, p<0.05 at each time point.
Figure 2:
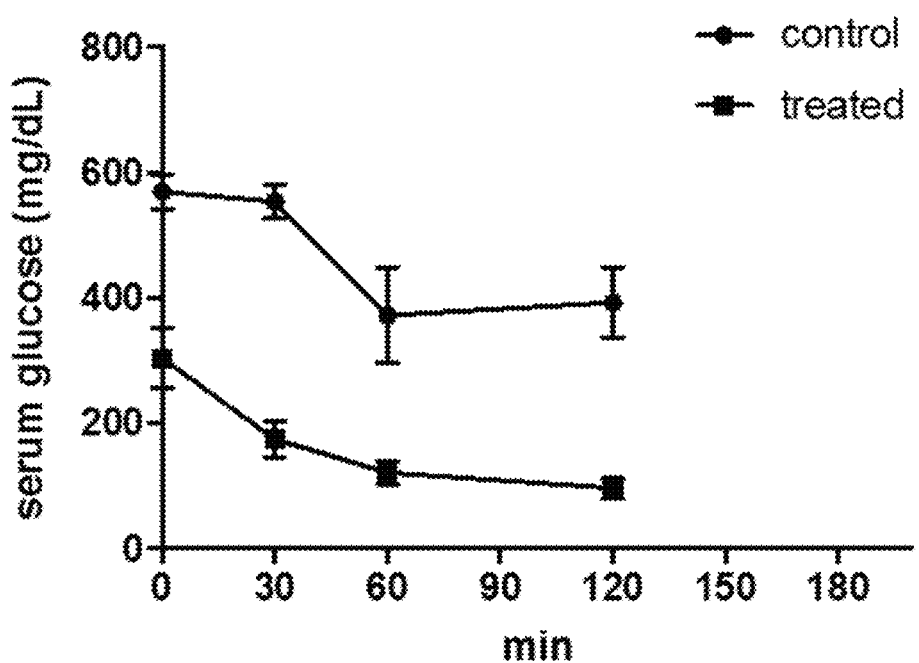
FIG. 2 illustrates an insulin sensitivity test. Mice treated with miR-29 mimics showed reduced serum glucose levels after fasting (time 0) and after injection of insulin, compared to untreated control animals. N=5, p<0.05 at each time point.
Figure 3:
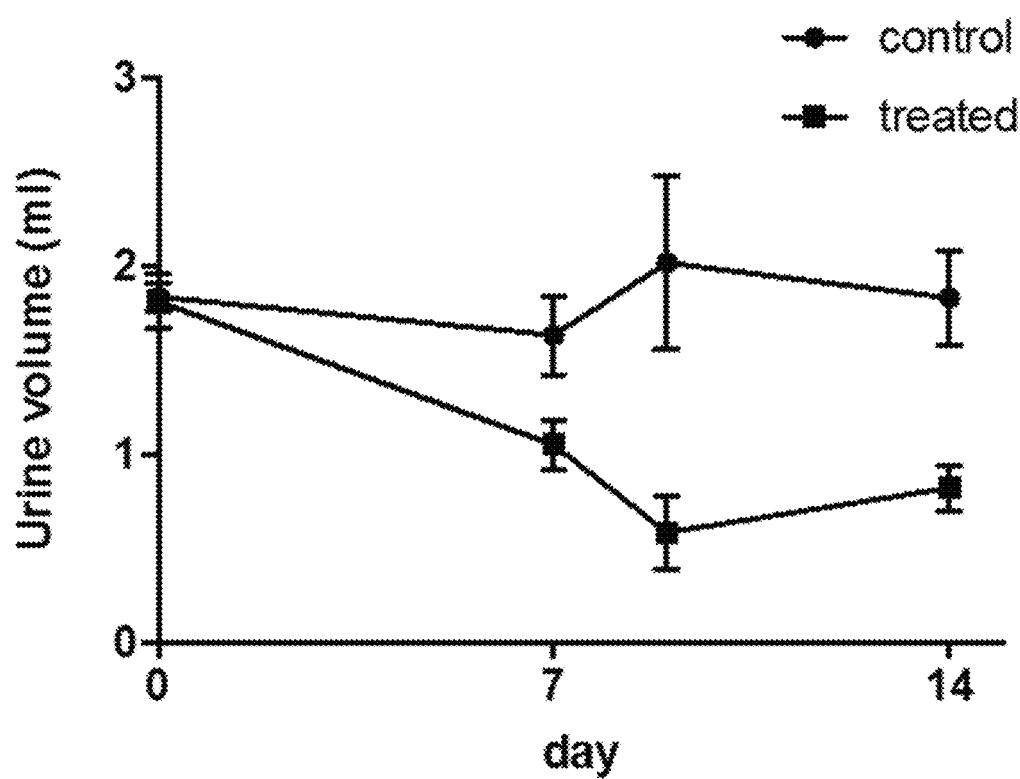
FIG. 3 illustrates 24-hour urine volume (ml). Mice treated with miR-29 mimics showed reduced urinary volume compared to untreated control animals. N=5, p<0.05.
Figure 4:
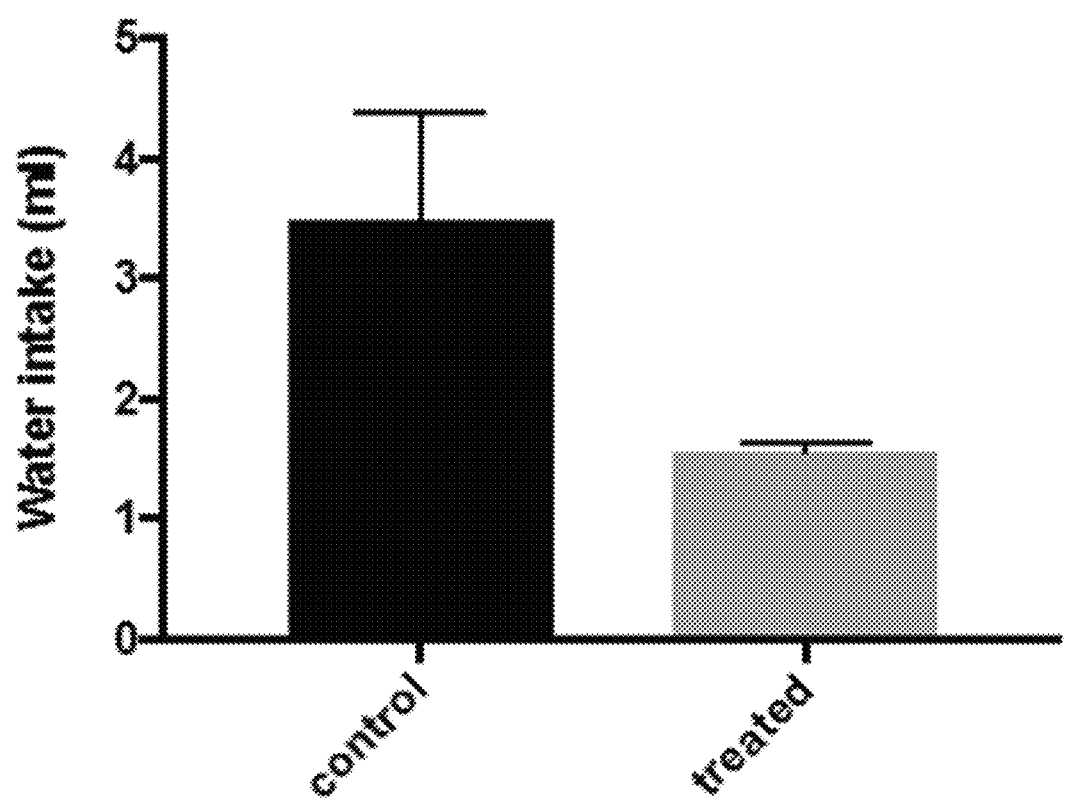
FIG. 4 illustrates 24-hour water intake levels (ml). Mice treated with miR-29 mimics showed reduced water intake levels compared to untreated control animals. N=5, p<0.05.
Figure 5:
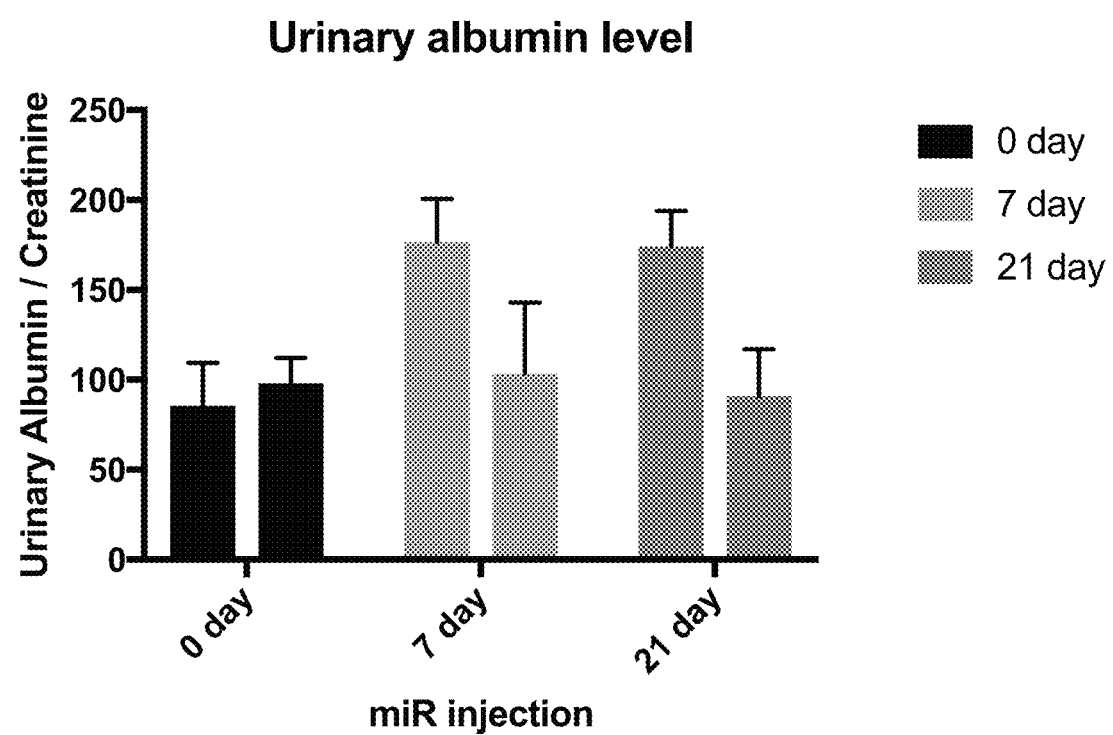
FIG. 5 illustrates 24-hour urinary albumin levels. Mice treated with miR-29 mimics showed reduced urinary albumin levels after 21 days of treatment compared to untreated control animals. N=5, p<0.05.

The present disclosure is based, at least in part, on the discovery that administration of miR-29 mimics into a db/db mouse can reverse hyperglycemia, insulin resistance, and albuminuria, hallmarks of diabetes mellitus (DM) and diabetic nephropathy (DN).

Metabolic Disorders

The present disclosure provides for the treatment of metabolic disorders (e.g., diabetic nephropathy, insulin resistance) using synthetic microRNAs (miRNAs or miRs).

Diabetes mellitus (DM) is a metabolic disorder manifested by high serum glucose levels and is associated with chronic microvascular complications. DM can be caused by insulin deficiency (commonly known as type I DM) or by insulin resistance (commonly known as type II DM).

Insulin resistance can be defined as a condition in which cells cannot respond to insulin, either endogenously produced or exogenously administered, in peripheral tissues including liver, adipose, and skeletal muscle. Insulin resistance is not associated with the insulin (INS) gene expression or protein production.

Instead, insulin resistance is caused by defects in the insulin receptor (INSR) gene. Genetic mutations in the INSR gene can cause severe insulin resistance syndromes, including leprechaunism, Rabson-Mendenhall syndrome, or type-A syndrome of insulin resistance. Reduced expression of the INSR gene can also cause insulin resistance in various forms of insulin-resistant diabetes mellitus.

Insulin resistance is frequently treated with metformin. Metformin's main effect is to decrease liver glucose production (hepatic gluconeogenesis). It also increases insulin receptor sensitivity, which increases peripheral glucose uptake in adipose tissue and skeletal muscle. The average patient with insulin resistance has three or more times the normal rate of gluconeogenesis. Metformin treatment reduces this by over one-third.

Diabetic nephropathy (DN) is characterized by glomerular hyperfiltration, mesangial hypertrophy, and microalbuminuria due to hemodynamic perturbations in glomerular vasculature. Glomerular hyperfiltration in DM predisposes patients to progressive damage to glomerular filtration by increasing the hydraulic pressure ($P_{GLO}$) and the permeability of macromolecules such as albumin across the glomerular filtration barrier (GFB). Reducing the renal vascular tone by interruption of the renin-angiotensin system with losartan has been approved to halt the progression of clinical DN.

Diabetic nephropathy (DN) due to insulin resistance affects millions of patients. There is currently no effective treatment and often patients will need a kidney transplant.

Described herein is the utility of a new treatment method based upon administration of microRNA (e.g., via injection). This approach is effective and easy to deliver and has low toxicity. This approach can be useful in treating insulin resistance, type II diabetes, or diabetic nephropathy.

Models of Metabolic Disease

The db/db mouse is an industry-accepted model of metabolic disease (e.g., insulin resistance, diabetic nephropathy) where the leptin receptor is deficient because the mice are homozygous for a point mutation in the gene encoding the leptin receptor (Lep-R). As described herein, the db/db mouse was treated with a composition comprising miR-29 mimics. Treatment with the miR-29 mimic composition corrected a wide spectrum of diabetic nephropathy phenotypes including albuminuria and polyuria, in addition to insulin resistance and hyperglycemia.

The db/db mouse can be used as a model of insulin resistance, diabetic nephropathy, type II diabetes, diabetic dyslipidemia, or metabolic syndrome.

The db/db mouse has an autosomal recessive mutation in the Leprdb gene on chromosome 4. This mutation results in several phenotypes, including obesity that develops at 4-5 weeks of age, plasma insulin that is elevated at 10-14 days, polyphagia, proteinuria, glycosuria, polyuria/polydipsia, hyperinsulinemia despite severe depletion of pancreatic islet insulin-producing β-cells, leptin receptor deficiency, and hyperglycemia that develops at 4-8 weeks of age.

MicroRNA (miRNA) Mimics

The present disclosure describes chemically modified synthetic miR-29 mimic molecules and their use in correcting diabetic nephropathy (DN) and insulin resistance. As described herein, administration of miR-29 mimics to the db/db mouse can correct diabetic nephropathy including albuminuria and insulin resistance characterized by hyperglycemia.

The present disclosure provides for the identification of effective miR-29 mimic molecules; methods for conjugating miR-29 mimics with carrier molecules, and dose and duration for intravenous (I.V.) injection route of miR-29 mimic molecules in mice. After injection of miR-29 mimics, diabetic nephropathy in mice is improved, including reduction in albuminuria and urine volume, reduction in water intake, improvement in glucose tolerance test, and improvement in insulin tolerance test.

Example 1 describes how the administration of miR-29 mimics can increase the gene expression levels of insulin receptor (INSR) in peripheral tissues including liver, adipose, and skeletal muscle, as direct evidence of improving insulin receptor sensitivity (e.g., reversing insulin resistance). Example 1 further provides for the identification of effective miR-29 mimic molecules, methods for conjugating miR-29 mimics with carrier molecules, and dose and duration for intravenous injection route of miR-29 mimic molecules in mice. After injection of miR-29 mimics, db/db mice show a reduction in serum glucose level, reduction in water intake, reduction in urine glucose level, reduction in urine volume, reduction in urinary albumin levels, improvement in glucose tolerance test, and improvement in insulin sensitivity test.

miR-29 Genes

The miR-29 gene family consists of three members (miR-29a, miR-29b and miR-29c) which are encoded by two distinct genomic loci (a/b1 and b2/c) in both human and rodent genomes. The miR-29a and b1 genes are clustered into the a/b1 locus and share the same promoter, while miR-29b2 and c genes are primed from the b2/c locus using a single promoter. As all members have the same seed binding sequence, they all bind to the same set of target genes. The human and rodent miR-29 gene sequences are identical.

Nucleotide Sequences miR-29 mimics

Working strand sequence: UAGCACCAUCUGAAAUCGGUUUU (SEQ ID NO: 1)

Passenger strand sequence: AACCGAUUUCuuuUGGUGCUAUU (SEQ ID NO: 2)

The passenger strand comprises the following modifications:
1. 2'-O-methylation modification to increase stability
2. cholesterol can be conjugated to the 3'-end to enhance cellular uptake miR-29a
UAGCACCAUCUGAAAUCGGUUA (SEQ ID NO: 3)
miR-29b
UAGCACCAUUUGAAAUCAGUGUU (SEQ ID NO: 4)
miR-29c
UAGCACCAUUUGAAAUCGGUUA (SEQ ID NO: 5)

Carrier Molecule

A carrier molecule can be a polycationic polymer or amphiphilic non-viral carrier. For example, the carrier can be a polyethylenimine (PEI). As another example, the PEI can be a low-MW PEI derivative with degradable linkages, including ester, disulfide, imine, carbamate, amide, or ketal linkages As described herein, the carrier described in Example 1, can be a polyethylenimine, branched, MW: 25 kDa, CAS No: 9002-98-6, and has a linear formula: $H(NHCH_2CH_2)_nNH_2$.

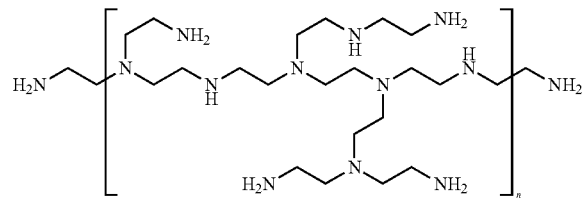

Conjugation

Polyethylenimine and miR-29 mimic can be mixed at the N/P ratio of 0.8 ('N/P' refers to the ratio of the nitrogens of the polyethylenimine and the phosphate groups of the nucleic acid). The polyplexes are dissolved in 0.5% glucose solution and administered to a subject.

Therapeutic Methods

Also provided is a process of treating a metabolic disorder in a subject in need thereof comprising administration of a therapeutically effective amount of a miR-29 mimic, so as to reverse hyperglycemia, reverse insulin resistance, reverse albuminuria, correct albuminuria, correct polyuria, correct glucose tolerance, correct insulin tolerance, reduce urine output of a subject, reduce serum glucose levels of a subject, reduce insulin sensitivity of a subject, reduce urinary albumin levels of a subject, reverse symptoms associated with diabetes mellitus (DM) and diabetic nephropathy (DN), reduce albuminuria, reduce urine volume, reduce water intake, improve glucose tolerance test, or improve insulin tolerance test.

Methods described herein are generally performed on a subject in need thereof. A subject in need of the therapeutic methods described herein can be a subject having, diagnosed with, suspected of having, or at risk for developing a metabolic disorder. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans. For example, the subject can be a human subject.

Generally, a safe and effective amount of a miR-29 mimic is, for example, that amount that would cause the desired therapeutic effect in a subject while minimizing undesired side effects. In various embodiments, an effective amount of a miR-29 mimic described herein can substantially inhibit a metabolic disorder, slow the progress of a metabolic disorder, or limit the development of a metabolic disorder.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a miR-29 mimic can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to reverse hyperglycemia, reverse insulin resistance, reverse albuminuria, correct albuminuria, correct polyuria, correct glucose tolerance, correct insulin tolerance, reduce urine output of a subject, reduce serum glucose levels of a subject, reduce insulin sensitivity of a subject, reduce urinary albumin levels of a subject, reverse symptoms associated with DM and DN, reduce albuminuria, reduce urine volume, reduce water intake, improve glucose tolerance test, or improve insulin tolerance test.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a miR-29 mimic can occur as a single event or over a time course of treatment. For example, a miR-29 mimic can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for a metabolic disorder.

A miR-29 mimic can be administered simultaneously or sequentially with another agent, such as an antibiotic, an anti-inflammatory, or another agent. For example, a miR-29 mimic can be administered simultaneously with another agent, such as an antibiotic or an anti-inflammatory. Simultaneous administration can occur through administration of separate compositions, each containing one or more of a miR-29 mimic, an antibiotic, an anti-inflammatory, or another agent. Simultaneous administration can occur through administration of one composition containing two or more of a miR-29 mimic, an antibiotic, an anti-inflammatory, or another agent. A miR-29 mimic can be administered sequentially with an antibiotic, an anti-inflammatory, or another agent. For example, a miR-29 mimic can be administered before or after administration of an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

For example, Example 1 describes administration route, dosage and duration. MiR-29 mimics are injected intravenously (I.V.), at 1 mg/kg body weight, once per day for 14 days.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to miRNA mimics, miRNA, or carriers. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: miR-29 Mimics and Uses Thereof for Treatment of Diabetes Mellitus and Diabetic Nephropathy This example describes a pharmaceutical composition comprising chemically modified synthetic miR-29 (e.g., miR-29 mimic). For example, the pharmaceutical composition comprises miR-29 mimics and carrier molecules. This example describes the mimics and their use in reversing diabetes mellitus (DM) and diabetic nephropathy (DN).

The present disclosure is based, at least in part, on the discovery that administration of miR-29 mimics into a db/db mouse can reverse hyperglycemia, insulin resistance, and albuminuria, hallmarks of DM and DN.

Metabolic Disease Model

The db/db mouse is an industry-accepted model of obesity, insulin resistance, and dyslipidemia in which the leptin receptor is deficient because the mice are homozygous for a point mutation in the gene encoding the leptin receptor (Lep-R). Similar mutations in the human Lep-R gene have been shown to cause obesity and insulin resistance.

As shown here, administration of miR-29 mimics can increase the gene expression levels of insulin receptor (INSR) in peripheral tissues including liver, adipose, and skeletal muscle, as direct proof of improving insulin receptor sensitivity, e.g., reversing insulin resistance.

This example describes the identification of effective miR-29 mimic molecules; methods for conjugating miR-29 mimics with carrier molecules; and dose and duration for I.V. injection route of miR-29 mimic molecules in mice.

After injection of miR-29 mimics, data showed a reduction in serum glucose level, reduction in water intake, reduction in urine glucose level, reduction in urine volume, reduction in urinary albumin levels, improvement in glucose tolerance test, and improvement in insulin sensitivity test.

MiR-29 Genes

The miR-29 gene family consists of three members (miR-29a, miR-29b and miR-29c), which are encoded by two distinct genomic loci (a/b1 and b2/c) in both human and rodent genomes. The miR-29a and b1 genes are clustered into the a/b1 locus and share the same promoter, while miR-29b2 and c genes are primed from the b2/c locus using a single promoter. As all members have the same seed binding sequence, they all bind to the same set of target genes. The human and rodent miR-29 gene sequences are identical.

MiR-29 MIMICS

Working strand sequence: UAGCACCAUCUGAAAUCGGUUUU (SEQ ID NO: 1)

Passenger strand sequence: AACCGAUUUCuuuUGGUGCUAUU (SEQ ID NO: 2)

The passenger strand comprises the following modifications:

1. 2'-O-methylation modification to increase stability
2. cholesterol can be conjugated to the 3'-end to enhance cellular uptake MiR-29 Nucleotide Sequences MiR-29a: UAGCACCAUCUGAAAUCGGUUA (SEQ ID NO: 3)

MiR-29b: UAGCACCAUUUGAAAUCAGUGUU (SEQ ID NO: 4)

MiR-29c: UAGCACCAUUUGAAAUCGGUUA (SEQ ID NO: 5)

Carrier Molecule

Polyethylenimine, branched, MW: 25 kDa, CAS No: 9002-98-6, Linear formula: $H(NHCH_2CH_2)_nNH_2$.

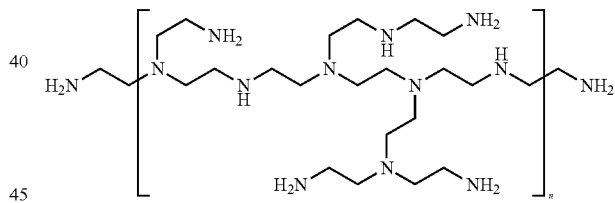

Conjugation

Polyethylenimine and miR-29 mimic are mixed at the N/P ratio of 0.8 ('N/P' refers to the ratio of the nitrogens of the polyethylenimine and the phosphate groups of the nucleic acid). The polyplexes are dissolved in 0.5% glucose solution and administered to animals.

Administration Route, Dosage, and Duration

MiR-29 mimics are injected via I.V., at 1 mg/kg body weight, once per day for 14 days.

What is claimed is:

1. A method of increasing gene expression levels of insulin receptor (INSR) in a subject having a metabolic comprising administering to the subject, by injection, a therapeutically effective amount of a pharmaceutical composition comprising a miR-29 mimic molecule, wherein
   the miR-29 mimic molecule comprises a nucleotide sequence comprising SEQ ID NO: 1, miR-29a (SEQ ID NO: 3), miR-29b (SEQ ID NO: 4), or miR-29c (SEQ ID NO: 5) and increases INSR gene expression activity.

2. The method of claim 1, wherein the miR-29 mimic molecule comprises:
   a working strand sequence comprising SEQ ID NO: 1; and
   a passenger strand, wherein the passenger strand optionally comprises SEQ ID NO: 2.

3. The method of claim 2, wherein the passenger strand comprises a modification to increase stability or a modification to enhance cellular uptake.

4. The method of claim 3, wherein the modification to increase stability comprises 2'-O-methylation.

5. The method of claim 3, wherein the modification to enhance cellular uptake comprises a cholesterol conjugated to the 3'-end of the passenger strand.

6. The method of claim 1, comprising a carrier conjugated to the miR-29 mimic molecule.

7. The method of claim 6, wherein the carrier comprises a polyethylenimine (PEI), a polycationic polymer, or amphiphilic non-viral carrier.

8. The method of claim 1, wherein the subject has a metabolic disorder selected from diabetic nephropathy (DN), diabetes mellitus (DM), insulin deficiency, or insulin resistance.

9. The method of claim 1, wherein the therapeutically effective amount corrects albuminuria, corrects polyuria, corrects glucose tolerance, or corrects insulin tolerance in the subject.

10. The method of claim 1, wherein the therapeutically effective amount reduces water intake, reduces urine output, reduces serum glucose levels, reduces insulin sensitivity, or reduces urinary albumin levels in a subject.

11. The method of claim 8, wherein the metabolic disorder does not comprise diabetic fibrosis.

* * * * *

SEQUENCE LISTING

```
<160> NUMBER OF SEQ ID NOS: 5

<210> SEQ ID NO 1
<211> LENGTH: 23
<212> TYPE: RNA
<213> ORGANISM: Artificial Sequence
<220> FEATURE:
<223> OTHER INFORMATION: miRNA mimic
```

```
<400> SEQUENCE: 1
uagcaccauc ugaaaucggu uuu                                          23

<210> SEQ ID NO 2
<211> LENGTH: 23
<212> TYPE: RNA
<213> ORGANISM: Artificial Sequence
<220> FEATURE:
<223> OTHER INFORMATION: miRNA mimic

<400> SEQUENCE: 2
aaccgauuuc uuuuggugcu auu                                          23

<210> SEQ ID NO 3
<211> LENGTH: 22
<212> TYPE: RNA
<213> ORGANISM: Homo sapiens

<400> SEQUENCE: 3
uagcaccauc ugaaaucggu ua                                           22

<210> SEQ ID NO 4
<211> LENGTH: 23
<212> TYPE: RNA
<213> ORGANISM: Homo sapiens

<400> SEQUENCE: 4
uagcaccauu ugaaaucagu guu                                          23

<210> SEQ ID NO 5
<211> LENGTH: 22
<212> TYPE: RNA
<213> ORGANISM: Homo sapiens

<400> SEQUENCE: 5
uagcaccauu ugaaaucggu ua                                           22
```